US009165387B2

(12) United States Patent
Gilbert

(10) Patent No.: US 9,165,387 B2
(45) Date of Patent: *Oct. 20, 2015

(54) GRAPHING DEVICE AND METHOD

(71) Applicant: BOSCH AUTOMOTIVE SERVICE SOLUTIONS INC., Warren, MI (US)

(72) Inventor: Harry M. Gilbert, Portage, MI (US)

(73) Assignee: Bosch Automotive Service Solutions Inc., Warren, MI (US)

( * ) Notice: Subject to any disclaimer, the term of this patent is extended or adjusted under 35 U.S.C. 154(b) by 182 days.

This patent is subject to a terminal disclaimer.

(21) Appl. No.: 13/785,915

(22) Filed: Mar. 5, 2013

(65) Prior Publication Data

US 2013/0300745 A1   Nov. 14, 2013

Related U.S. Application Data

(63) Continuation of application No. 12/762,840, filed on Apr. 19, 2010, now Pat. No. 8,392,053, which is a continuation-in-part of application No. 11/955,723, filed on Dec. 13, 2007, now Pat. No. 7,702,437.

(51) Int. Cl.
*G01M 17/00* (2006.01)
*G07C 5/00* (2006.01)
*G06T 11/20* (2006.01)
*G06F 19/00* (2011.01)

(52) U.S. Cl.
CPC .......... *G06T 11/206* (2013.01); *G06F 19/3406* (2013.01)

(58) Field of Classification Search
CPC ....... G07C 5/008; G07C 5/0808; F02D 41/22
USPC .......... 701/29, 31, 33–34; 709/217, 225, 245; 382/141; 600/300
See application file for complete search history.

(56) References Cited

U.S. PATENT DOCUMENTS

| 5,807,256 A | 9/1998 | Taguchi et al. |
| 2003/0018276 A1 | 1/2003 | Mansy et al. |
| 2005/0096561 A1 | 5/2005 | Conn et al. |
| 2006/0210141 A1 | 9/2006 | Kojitani et al. |
| 2006/0263833 A1 | 11/2006 | Loken et al. |

*Primary Examiner* — Mary Cheung
(74) *Attorney, Agent, or Firm* — Baker & Hostetler LLP

(57) ABSTRACT

To display patient information, a computing device receives a set of diagnostic values for a patient, a processor of the computing device compares the set of diagnostic values with a set of predetermined normal values, and a video image is displayed having a graphical depiction of the diagnostic values in comparison to the related normal values. The related set of normal values is displayed at a predetermined region of the video image and the set of diagnostic values is displayed on the video image in relation to the certain region of the normal values. Varying levels of relative health of the patient are indicated according the placement of an icon relative to areas of the graphical depiction of the diagnostic values. The video image is a plurality of concentric circles with the diagnostic values being displayed relatively closer to a center of the display in response to the diagnostic values being relatively closer to the values of the related normal values.

20 Claims, 10 Drawing Sheets

GRAPHING DEVICE AND METHOD

CROSS REFERENCE TO RELATED APPLICATIONS

This application claims benefit of and is a continuation of U.S. patent application Ser. No. 12/762,840 filed Apr. 19, 2010, now U.S. Pat. No. 8,392,053, which is a continuation-in-part of U.S. patent application Ser. No. 11/955,723, entitled "MULTIDIMENSIONAL VEHICLE HEALTH GRAPHICS," filed Dec. 13, 2007, both of which are hereby incorporated by reference in their entirety.

FIELD OF THE INVENTION

The present invention relates generally to a display. More particularly, the present invention relates to a method of displaying information and a display device.

BACKGROUND OF THE INVENTION

Onboard control computers have become prevalent in motor vehicles, but as safety, economy, and emissions requirements have continued to tighten, friction braking systems, and traction control devices have not met the requirements set out in government regulations and the implicit demands of competitors' achievements. Successive generations of onboard control computers have acquired increasing data sensing and retention capability as the electronics have advanced.

Present external diagnostic and display apparatus, known as diagnostic tools, are commonly limited to reporting the data acquired by the onboard control computer itself. Increasingly, subtle subsystem failures in vehicles overload the ability of maintenance technicians, not simply to read the faults detected and stored by the diagnostic tools themselves, but to combine those readings with peripheral measurements and deduce corrective actions with both speed and accuracy.

Currently in the automotive industry, there are both stand alone and hand-held diagnostic testers or tools used in connection with motor vehicle maintenance and repair. For example, hand-held diagnostic tools have been used to trouble-shoot faults associated with vehicular control units. Diagnostic tools detect faults based on Diagnostic Trouble Codes or DTCs that are set in the vehicle's onboard control computer. A DTC can be triggered and stored when there is a problem with the vehicle. A technician then retrieves the DTC using a diagnostic tool, repairs the associated problem and then deletes the DTC from the vehicle's computer.

Vehicle diagnostics have also been performed through personal computers. However, the display of such diagnostic information has always been difficult to read for technicians. Furthermore, technicians have also needed extensive learning in order to read such diagnostic information.

Further general vehicle health information have also be monitored through personal computers, or standalone computing modules that measure information related to emission testing. Certain sensors are attached to the vehicle to make certain measurements related to environmental emissions or safety related information of the vehicle.

The current diagnostic tools and personal computers used for vehicle diagnostics and vehicle health information are limited in the display output, thus limiting the usefulness of the diagnostic tool for a user. The limits on the current tools output capabilities include, for example, problems with the method of indicating the DTC, or vehicle health information such as the measurement of a certain sensors in the vehicle.

The current diagnostic tools show the DTC on a basic display that displays the basic information and such information, then must be checked manually or through additional steps to ascertain whether the information is within the normal limits. The user must be in close proximity and in viewing distance from the diagnostic tool as the information is usually text based. For example, when a diagnostic tool detects a DTC or an emission testing result, a user must directly view the tool in order to see the DTC or emission testing readout.

The user of the diagnostic tool can be forced to use additional devices in order to supplement the limitations of output methods of today's diagnostic tools or personal computers used for diagnostic purposes. Accordingly, it is desirable to provide a method and apparatus that will allow enhanced display capabilities to a user or technician to use a diagnostic tool or diagnostic personal computer to determine the output of the vehicle's health information in a manner that is easy and quick to ascertain whether it is within normal constraints.

Similarly, in the medical industry, conventional displays are often difficult to quickly interpret. This problem may be exacerbated when multiple diagnostic values are displayed simultaneously on a single display. The alternative of having multiple displays may slow interpretation time as well as limit how small the display can be made. Accordingly, it is desirable to provide a display device and method of display that is capable of overcoming the disadvantages described herein at least to some extent.

SUMMARY OF THE INVENTION

The present invention provides, in some embodiments, a display device and method of display that is capable of overcoming the disadvantages described herein at least to some extent.

An embodiment of the present invention pertains to a method of displaying information. In this method, a computing device receives a set of diagnostic values for a patient, a processor of the computing device compares the set of diagnostic values with a set of predetermined normal values, and a video image is displayed having a graphical depiction of the diagnostic values in comparison to the related normal values. The related set of normal values is displayed at a predetermined region of the video image and the set of diagnostic values is displayed on the video image in relation to the certain region of the normal values. Varying levels of relative health of the patient are indicated according the placement of an icon relative to areas of the graphical depiction of the diagnostic values. The video image is a plurality of concentric circles with the diagnostic values being displayed relatively closer to a center of the display in response to the diagnostic values being relatively closer to the values of the related normal values.

Another embodiment of the present invention relates to an apparatus for displaying a patient's diagnostic values. The apparatus including a communication interface, a memory, a processor, a display, and an icon. The communication interface is to receive the diagnostic values. The memory is to store a set of computer executable instructions for displaying of the diagnostic values. The processor is connected to the memory and is configured to execute the set of computer executable instructions. In response to the set of computer executable instructions the processor is configured to compare the diagnostic values with a set of predetermined normal values. The display displays a video image having a graphical depiction of the diagnostic values in comparison to the normal values. The icon is configured to indicate varying levels of relative health of the patient and positioned on the graphical depiction of the diagnostic values. The video image is a plurality of concentric circles, with the diagnostic values being displayed relatively closer to center in response to the diagnostic values being relatively closer to values of the related normal values.

Yet another embodiment of the present invention pertains to a system for displaying a set of diagnostic values from a patient. The system includes a means for receiving, a means for comparing, a means for displaying, and an icon. The means for receiving receives the diagnostic values. The means for comparing compares the set of diagnostic values with a set of predetermined normal values. The means for displaying displays a video image having a graphical depiction of the diagnostic values in comparison to the normal values. The icon is configured to indicate varying levels of relative health of the patient and positioned on the graphical depiction of the measured set values. The video image is a plurality of concentric circles with diagnostic values of the patient being displayed relatively closer to a center of the means for display in response to the diagnostic values being relatively closer in value to the related normal values.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

Figure 1:
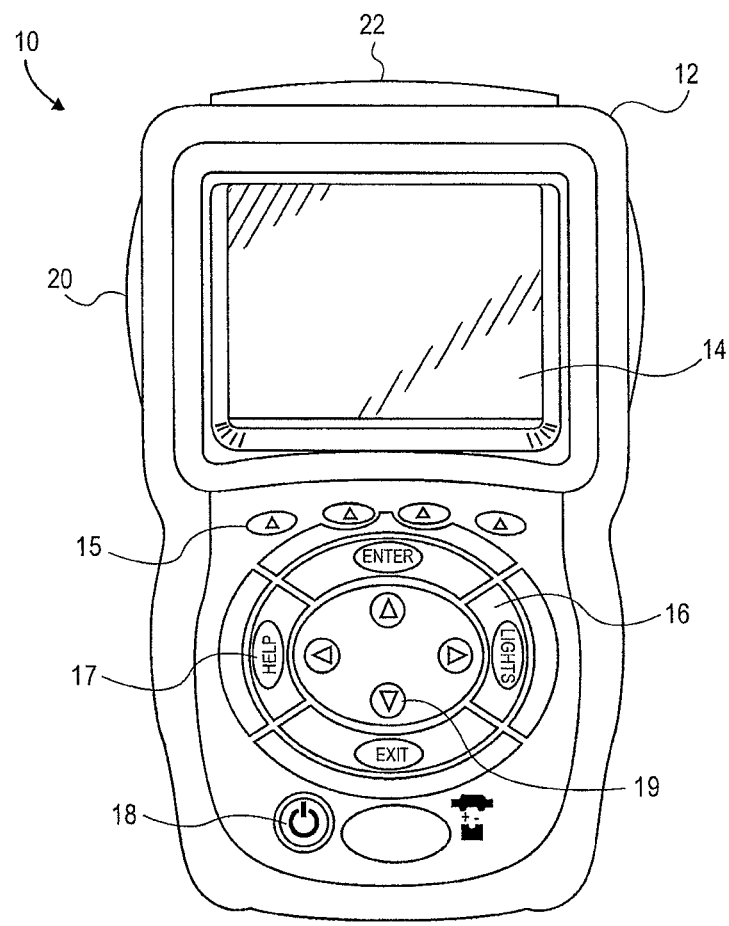
FIG. 1 is a front view of a diagnostic tool with a display.

The invention will now be described with reference to the drawing figures, in which like reference numerals refer to like parts throughout. An embodiment in accordance with the present invention provides an efficient means of displaying and ascertaining from the display the relative health of a vehicle in relation to normal outputs. This invention proposes a visual health display which permits the technician to see at a glance the relative health of a vehicle system, and where the most serious problems are.

Manufacturers have programmed their vehicle onboard computers with complicated methods of detecting a variety of problems. Further, the United States Environmental Protection Agency has mandated that DTCs be set where there are emissions related problems with the vehicle using the Onboard Diagnostic II System, also known as the OBD II system.

However, there are still problems of using the diagnostic tool since there are limitations in the output methods of the diagnostic tool or personal computer or other computing device used to display the vehicle's health output. A user is forced to look at the display with the current vehicle health information and then go through addition steps such as looking through manuals or checking through another menu on the display to ascertain the normal outputs of the vehicle and then have to ascertain whether the current outputs are within the normal constraints.

Normal constraints can be defined for example with a range of acceptable operation of a vehicle under certain predetermined circumstances. The range of normal values can be a set of values, for example, for the same type vehicle when it is functioning under universally acceptable standards, or under a certain set of standards that are preset by, for example, by a board. For example, normal constraints for the values can be set by a vehicle's emission board or according to state law to what are acceptable measured values.

In an embodiment of the present invention, the diagnostic tool or computer will run an application that accommodates a display of images that will relay to the technician in an efficient manner the vehicles health information in relation to a base set of data that is considered the normal for a healthy vehicle.

An embodiment of the present inventive apparatus is illustrated in FIG. 1. In particular, FIG. 1 is a front view illustrating a diagnostic tool 10 according to an embodiment of the invention. The diagnostic tool 10 can be any computing device, for example, the NEMISYS diagnostic tool from SERVICE SOLUTIONS (part of the SPX Corporation). The diagnostic tool 10 includes a housing 12 to encase the various components of the diagnostic tool 10, such as a display 14, a user interface 16, a power button 18, a memory card reader 20 and a connector interface 22. The display 14 can be any type display, including for example but not limited to, a liquid crystal display (LCD), organic light emitting diode (OLED), field emission display (FED), electroluminescent display (ELD), etc. In addition, the LCD, for example, can be touch screen that both displays and performs the additional task of interfacing between the user and the diagnostic tool 10. The user interface 16 allows the user to interact with the diagnostic tool 10, in order to operate the diagnostic tool as the user prefers. The user interface 16 can include function keys, arrow keys or any other type of keys that can manipulate the diagnostic tool 10 in order to operate the diagnostic tool through the software. The user interface or input device 16 can also be a mouse or any other suitable input device for the user interface 16, including a keypad, touchpad, etc. The user interface 16 can also include keys correlating to numbers or alphanumeric characters. Moreover, as mentioned above, when the display 14 is touch sensitive, the display 14 can supplement or even substitute for the user interface 16. The power key or button 18 allows the user to turn the power to the diagnostic tool 10 on and off, as required.

A memory card reader 20 can be a single type card reader, such as, but not limited to, a compact flash card, floppy disk, memory stick, secure digital, flash memory or other type of memory. The memory card reader 20 can be a reader that reads more than one of the aforementioned memory such as a combination memory card reader. Additionally, the card reader 20 can also read any other computer readable medium, such as CD (compact disc), DVD (digital video or versatile disc), etc.

The connector interface 22 allows the diagnostic tool 10 to connect to an external device, such as, but not limited to, an ECU (electronic control unit) of a vehicle, a computing device, an external communication device (such as a modem), a network, etc. through a wired or wireless connection. Connector interface 22 can also include connections such as a USB (universal serial bus), FIREWIRE (Institute of Electrical and Electronics Engineers (IEEE) 1394), modem, RS232, RS48J, and other connections to communicate with external devices, such as a hard drive, USB drive, CD player, DVD player, or other computer readable medium devices.

Figure 2:
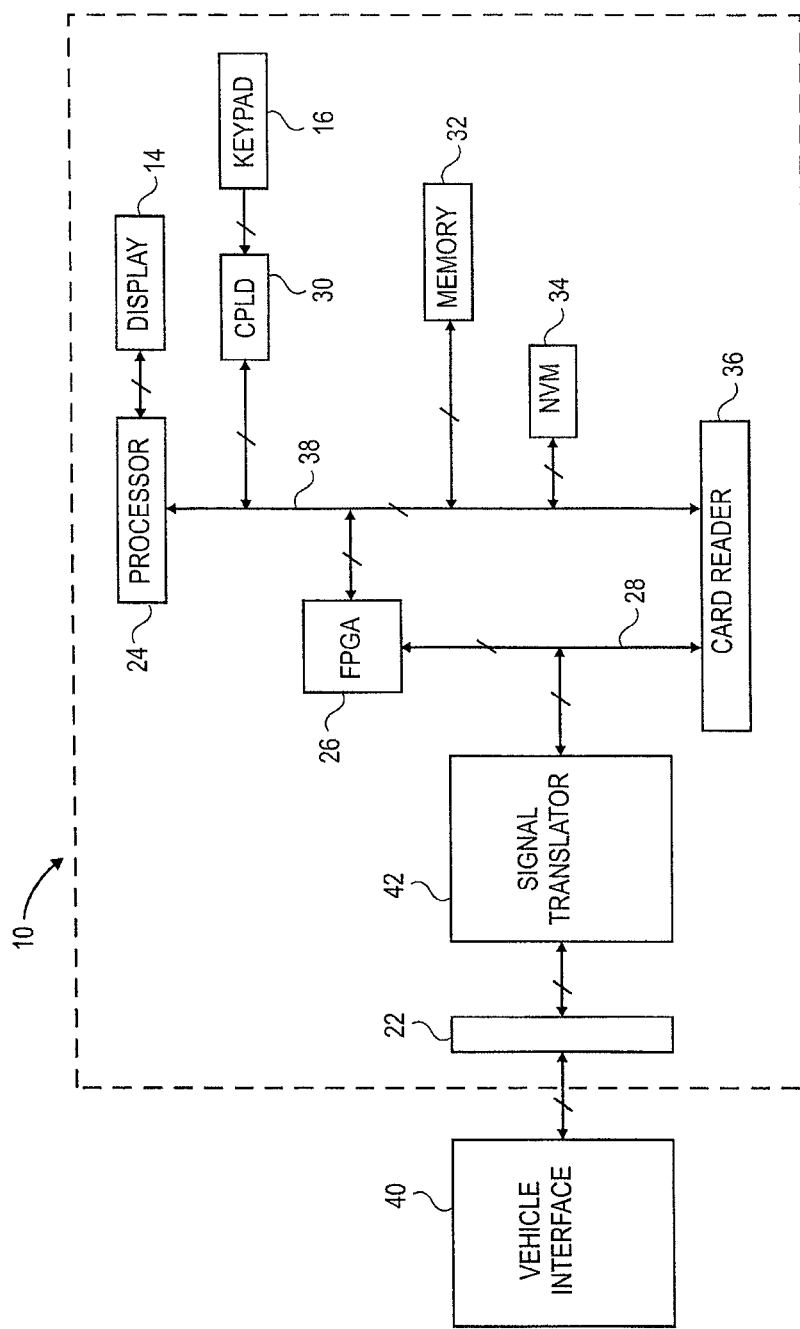
FIG. 2 is a schematic diagram of the diagnostic tool of FIG. 1.

FIG. 2 is a block diagram of the components of a diagnostic tool 10. In FIG. 2, the diagnostic tool 10, according to an embodiment of the invention, includes a processor 24, a field programmable gate array (FPGA) 26, a first system bus 28, the display 14, a complex programmable logic device (CPLD) 30, the user interface 16 in the form of a keypad, a memory subsystem 32, an internal non-volatile memory (NVM) 34, a card reader 36, a second system bus 38, the connector interface 22, and a selectable signal translator 42. A vehicle communication interface 40 is in communication with the diagnostic tool 10 through connector interface 22 via an external cable. The connection between the vehicle communication interface 40 and the connector interface 22 can also be a wireless connection such as BLUETOOTH, infrared device, wireless fidelity (WiFi, e.g. 802.11), etc.

The selectable signal translator 42 communicates with the vehicle communication interface 40 through the connector interface 22. The signal translator 42 conditions signals received from a motor vehicle control unit through the vehicle communication interface 40 to a conditioned signal compatible with the diagnostic tool 10. The translator 42 can communicate with, for example, the communication protocols of J1850 signal, ISO 9141-2 signal, communication collision detection (CCD) (e.g., Chrysler collision detection), data communication links (DCL), serial communication interface (SCI), S/F codes, a solenoid drive, J1708, RS232, controller area network (CAN), or other communication protocols that are implemented in a vehicle.

The circuitry to translate a particular communication protocol can be selected by the FPGA 26 (e.g., by tri-stating unused transceivers) or by providing a keying device that plugs into the connector interface 22 that is provided by diagnostic tool 10 to connect diagnostic tool 10 to vehicle communication interface 40. Translator 42 is also coupled to FPGA 26 and the card reader 36 via the first system bus 28. FPGA 26 transmits to and receives signals (i.e., messages) from the motor vehicle control unit through the translator 42.

FPGA 26 is coupled to the processor 24 through various address, data and control lines by the second system bus 38. FPGA 26 is also coupled to the card reader 36 through the first system bus 28. Processor 24 is also coupled to the display 14 in order to output the desired information to the user. The processor 24 communicates with the CPLD 30 through the second system bus 38. Additionally, the processor 24 is programmed to receive input from the user through the user interface 16 via the CPLD 30. The CPLD 30 provides logic for decoding various inputs from the user of diagnostic tool 10 and also provides the glue-logic for various other interfacing tasks.

Memory subsystem 32 and internal non-volatile memory 34 are coupled to the second system bus 38, which allows for communication with the processor 24 and FPGA 26. Memory subsystem 32 can include an application dependent amount of dynamic random access memory (DRAM), a hard drive, and/or read only memory (ROM). Software to run the diagnostic tool 10 can be stored in the memory subsystem 32. The internal non-volatile memory 34 can be, but not limited to, an electrically erasable programmable read-only memory (EEPROM), flash ROM, or other similar memory. The internal non-volatile memory 34 can provide, for example, storage for boot code, self-diagnostics, various drivers and space for FPGA images, if desired. If less than all of the modules are implemented in FPGA 26, the non-volatile memory 34 can contain downloadable images so that FPGA 26 can be reconfigured for a different group of communication protocols.

Figure 3:
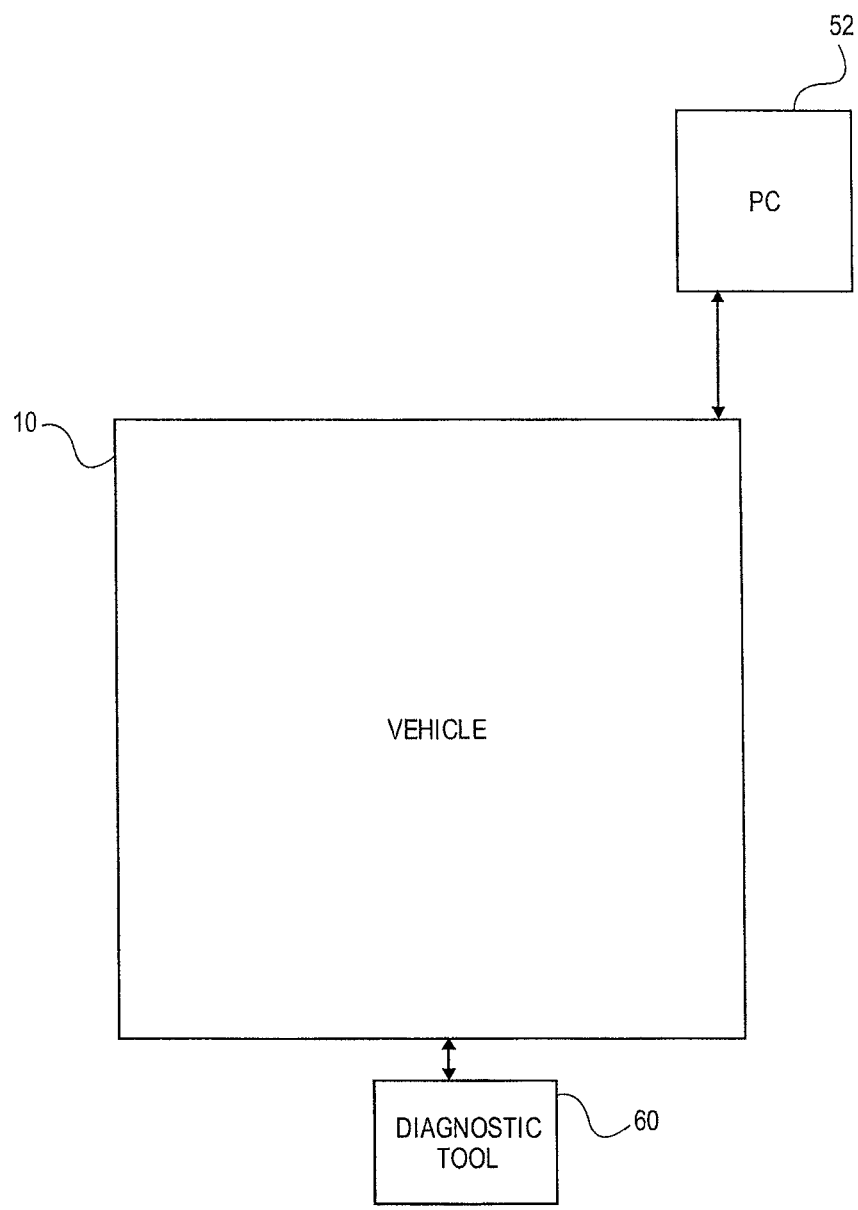
FIG. 3 is a block diagram of a diagnostic tool or personal computer connected to a vehicle for checking the health of a vehicle.

As seen in the block diagram of FIG. 3, diagnostic tool 10 can scan information of a vehicle 60. Vehicle diagnostic and health information can be ascertained through not only a computing device such as a diagnostic tool 60, but also a personal computer 52. If the distance is not too great, the IEEE 802.11 protocol or BLUETOOTH can be used to transfer information directly to the PC in a point-to-point connection or through a local area network.

Figure 4:
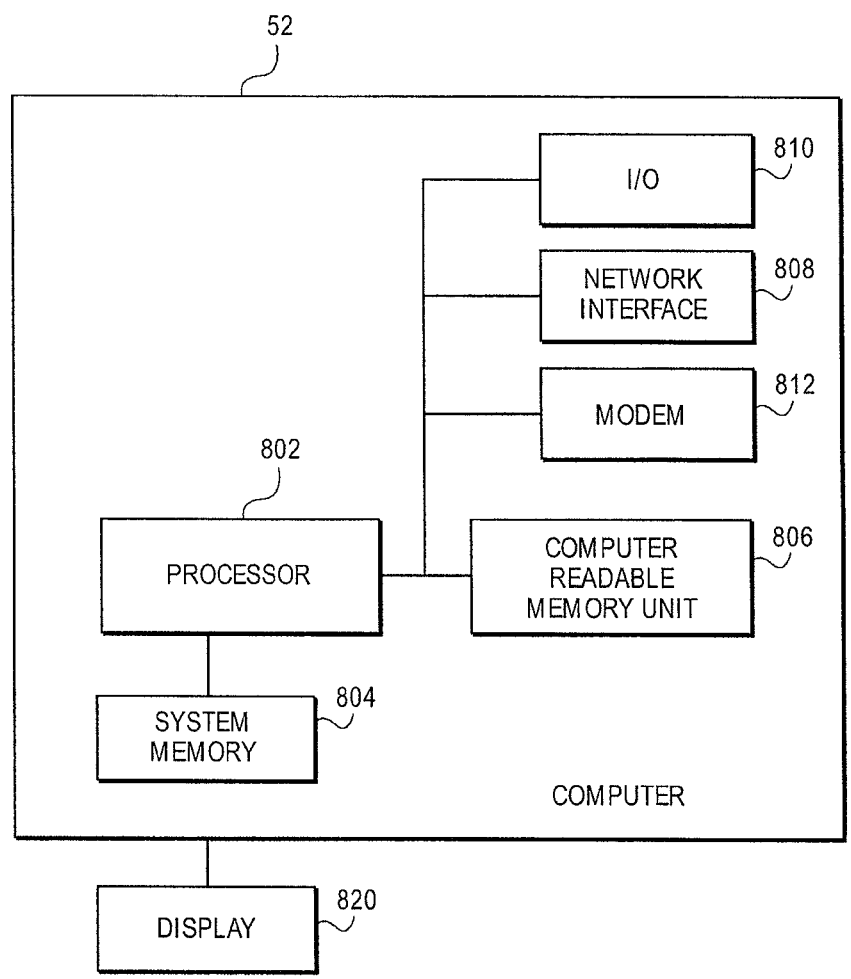
FIG. 4 is a schematic diagram of an exemplary computer that is capable of displaying the vehicle health graphics.

Referring to FIG. 4, an example of a computer, but not limited to this example of the computer 52, that can read computer readable media that includes computer-executable instructions. The computer 52 includes a processor 802 that uses the system memory 804 and a computer readable memory device 806 that includes certain computer readable recording media. A system bus connects the processor 802 to a network interface 808, modem 812 or other interface that accommodates a connection to another computer or network such as the Internet. The system bus may also include an input and output (I/O) interface 810 that accommodate connection to a variety of other devices. Furthermore, the computer 52 can output through, for example, the I/O 810, data for display on a display device 820.

Figure 5:
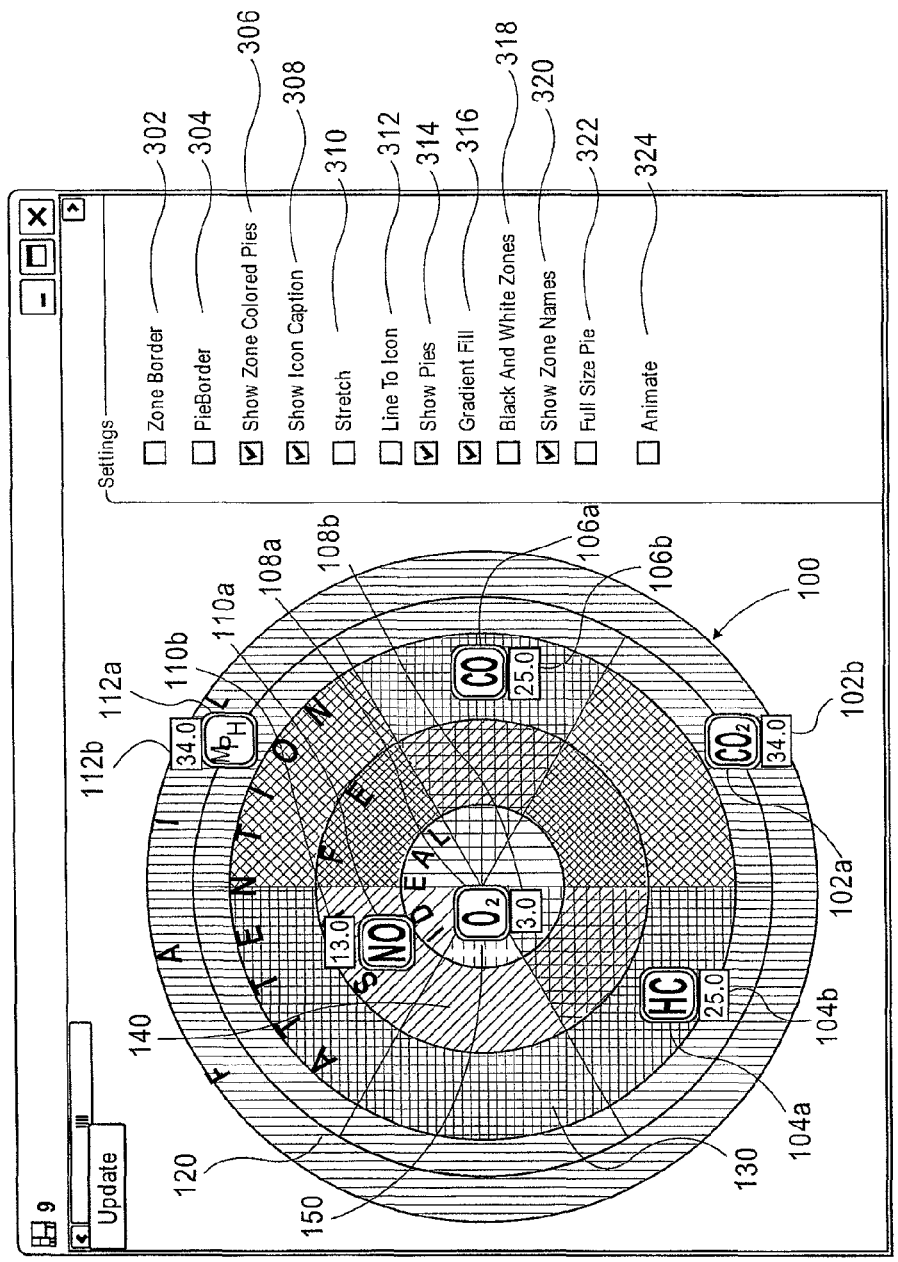
FIG. 5 is a graph of the vehicle health graphics on a display of a computing device such as personal computer or diagnostic tool depending on the selected options.

Referring to FIG. 5, for each vehicle there is a set of known good, or in-range, data values, such as engine coolant temperature, oxygen sensor, etc. In the present invention, a graphic image as seen in FIG. 5, such as a "bull's-eye" target 100, would be displayed as a background, with an icon 102a-112a for each reading of interest 102b-112b, respectively. The "bull's-eye" target 100 can also be described as a set of concentric circles.

The icons 102a-112a with the corresponding readings 102b-112b can be superimposed on the bulls-eye target 100 image. Further, the icons are located in a position that indicates the health of the vehicle 60.

For, example, if an engine temperature was in normal range, an icon for it would be displayed near or at the center of the "bull's-eye" image 100. As readings of these data approach the limits of failure, an icon representing the data will appear on a graphic display in a position to indicate that the value is sub-optimal. For example, a high engine temperature reading might show the temperature icon near the upper boundary of the "bull's-eye". The location of the icon within the "bull's eye" therefore is indicative of the relative health of the vehicle 60.

Additionally, the icons for sensors can themselves be replaced by icons for systems, groups of sensors, etc. The technician, or end-user can select items to track in this manner, or the selection can be done automatically.

The example in FIG. 5 shows readings from a vehicle, as might be seen during an emissions test. The icons are seen for gasses NO (110a), $O_2$ (108a), HC (104a), CO (106a) and $CO_2$ (102a), and the vehicle's speed (MPH) 112a while running a test on a dynamometer. The actual values shown are not representative of actual values for a vehicle. The reading (102b-112b) is the measurement being displayed, such as $O_2$ (Oxygen sensor) or MPH (Dynamometer velocity).

As seen in FIG. 5, there are different zones 120-150. Zones are used to describe the circular bands, or ranges, of values related to the Ideal range for a given reading. There may be as many zones as needed, or only a single one. The Ideal zone is in the center or concentric circle 150, while zone 120 at the periphery represent the opposite extreme, such as Worst Case, with surrounding zones 130-140 showing relationships to the central zone 150.

A zone does not necessarily represent an exact linear proportion to the whole circle, but is for visual effect. That is to say, the Ideal zone may represent a single value, say 0, while the Safe Zone may represent values from 1 to 100, the Attention zone may represent values from 101 to 110, and the Fail zone may represent any value above 110.

Each reading can have its own set of ranges (minimum, maximum, ideal). In the case where the center range (e.g., Ideal) is not the minimum or maximum value possible, the meter would display the value drifting back into the outer zones. That is to say, if the Ideal range for a reading is 100, readings of 90 and 110 might both appear in the same outer zones or might even appear in quite different zones, depending on the qualitative assessment of the value related to the ideal.

Zones may have colors associated with them to differentiate one zone from another or to show significance relative to the normal output. For example, White can be used for Ideal, Green for Safe, Yellow for Attention and Red for Fail correspond to common color schemes that have a universal significance to a technician without having to use a user's manual to figure out the significance of each color. Alternatively, the zone's color might not be used to color the zone band, but instead used to color the pie for a reading.

A pie is used to describe the triangular shapes which emanate from the center of the Health Meter to show the extent of the reading, or the zone that the reading is in, or both. Pies also demarcate the portion of the visual area occupied by a particular reading. Pies can be colored with a separate color for each reading, or can be colored depending upon the zone that the reading is currently in. Pies can be transparent (as in the attached examples) or opaque.

There are certain displayed options that can be available. The options of the test program which demonstrate the "Health Meter" of the invention as shown in FIG. 5, are seen on the right-hand side, and should clarify the options seen in the example of FIG. 5.

Figure 6:
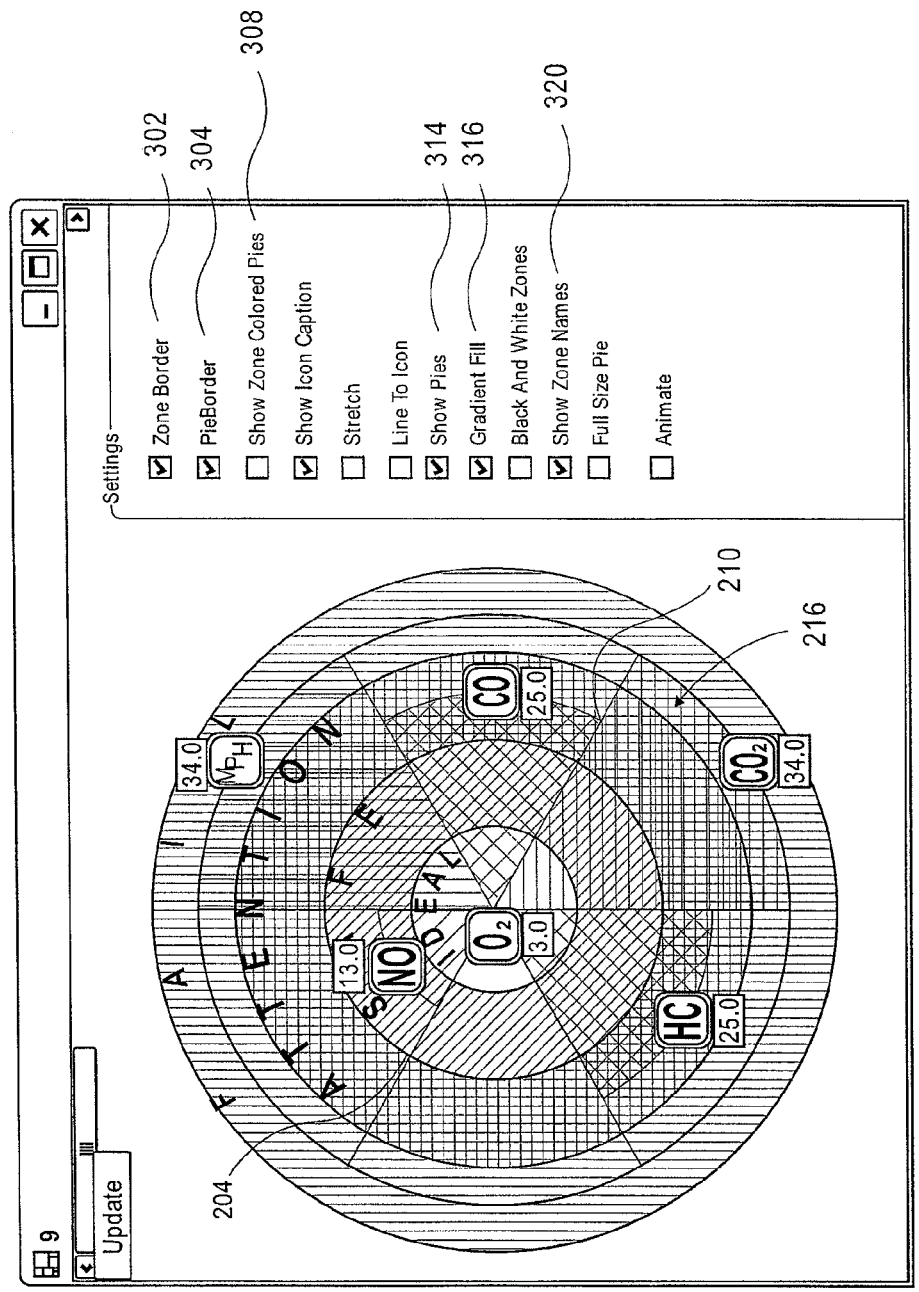
FIG. 6 is a graph of the vehicle health graphics on a display of a computing device such as personal computer or diagnostic tool depending on the selected options.

Referring to FIG. 6, the option 302 of the zone border 204 selects whether a zone has a bordering line or not. The zone border 204, for example, depending on the user or the displayed icons will aid in the technician ascertaining on which specific border the specific icon is displayed on.

As seen in FIG. 6, a pie border 210 option 304 selects whether a pie has a bordering line or not. A significance can be attached to the pie border. For example, the pie border can have the significance of a measurement being taken, or a region having secondary characteristics beyond the numerical value shown, such as a reading of 3.0, but that such a reading showed a large change over a space of time. For example, the radius of the pie can be time dependent with readings taken at time=0, can be shown at the top of the pie or readings taken at time=6 can be taken at the bottom of the pie. Other significance can be attached to the pie borders 210, and these were only shown as examples.

Referring to FIG. 5, the showing of the color the pies as seen in reference 210 being selected through the "Show Zone Colored Pies" 306 different than the color of the other pies, show to the color of the zone that the reading is in. Each color can have certain significance, such as certain colors for certain time dependent readings or other definitions can be attached to the color of the pie.

Referring to FIG. 5, "show icon caption" 308 illustrates the display of the value for the reading in a caption adjacent to the icon, as seen for example by 104a for HC as 25.0. The units for the measurements can also be displayed if requested or pre-programmed. The caption is moved for visibility purposes when it might be obscured or beyond the viewing area. Such a movement of the caption can be automatically obtained with the display.

Figure 7:
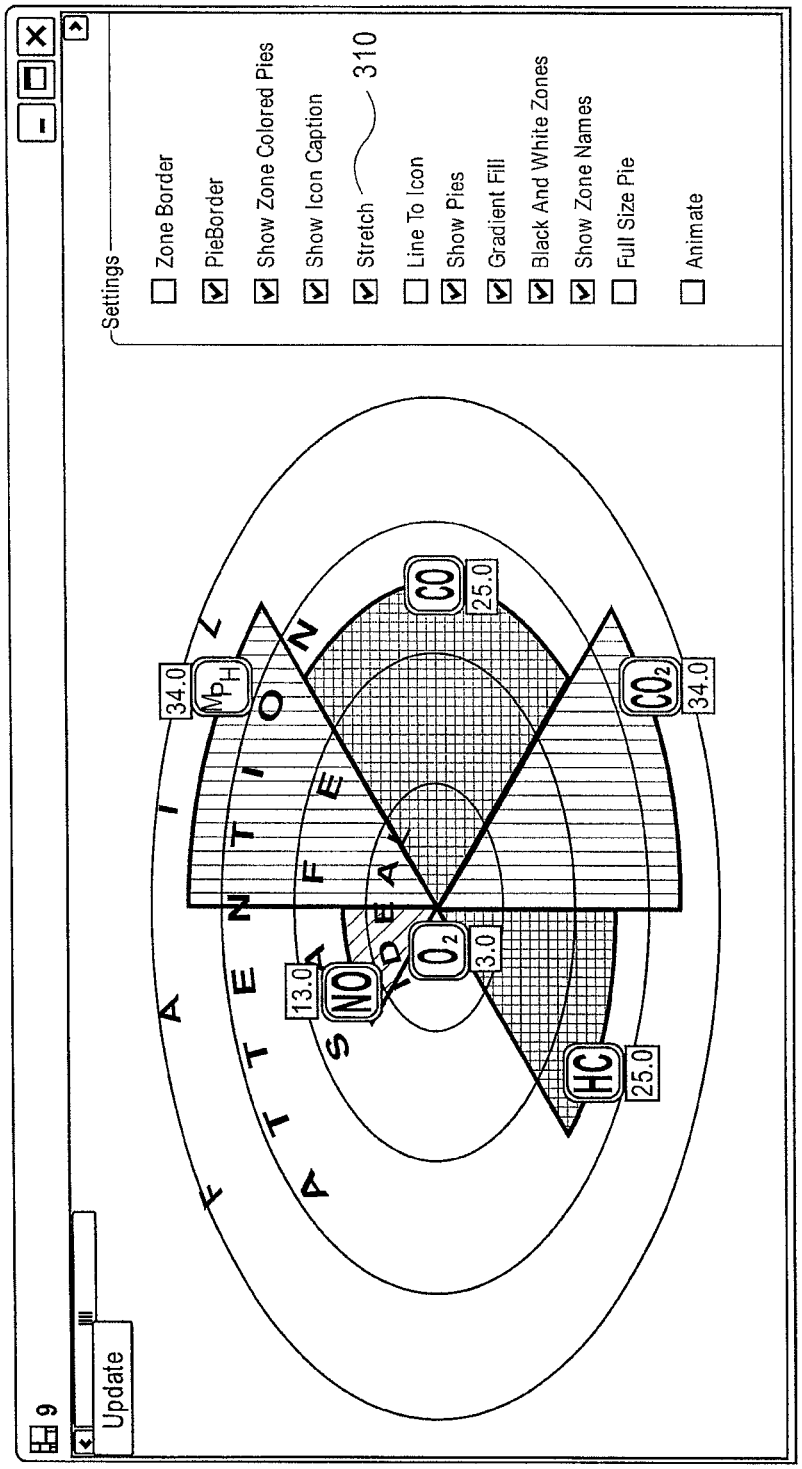
FIG. 7 is a graph of the vehicle health graphics on a display of a computing device such as personal computer or diagnostic tool depending on the selected options.

Referring to FIG. 7, the stretch option 310, illustrates the display area being distorted horizontally or vertically with no loss of content or visual features. This maybe necessary for a plurality of reasons, including having to display more than one image on a screen, and therefore, being able to stretch the view in any direction in order to accommodate the second screen, or to compensate for the screen size in order to maximize the displayed fonts, while allowing for the entire view.

The line to icon option 312 as illustrated by line 214, displays a single line is drawn from the center of the display area to the reading's position, such as 106a. The line to icon can, for example, help in the reading or following the different readings for a technician.

The show pies option 314 as shown by the pie 216 FIG. 6, has the pies for the readings. The showing of the pies 216 accommodates for a technician, for example, a greater differentiation between different pie areas, or pie zones, where each pie may have different significances.

The gradient fill option 316 is where the display is shown with 'shading' from light to dark as seen for example in FIG. 6. This again, allows for an easier reading of the information, especially if a technician is located a certain distance from the display screen.

Figure 8:
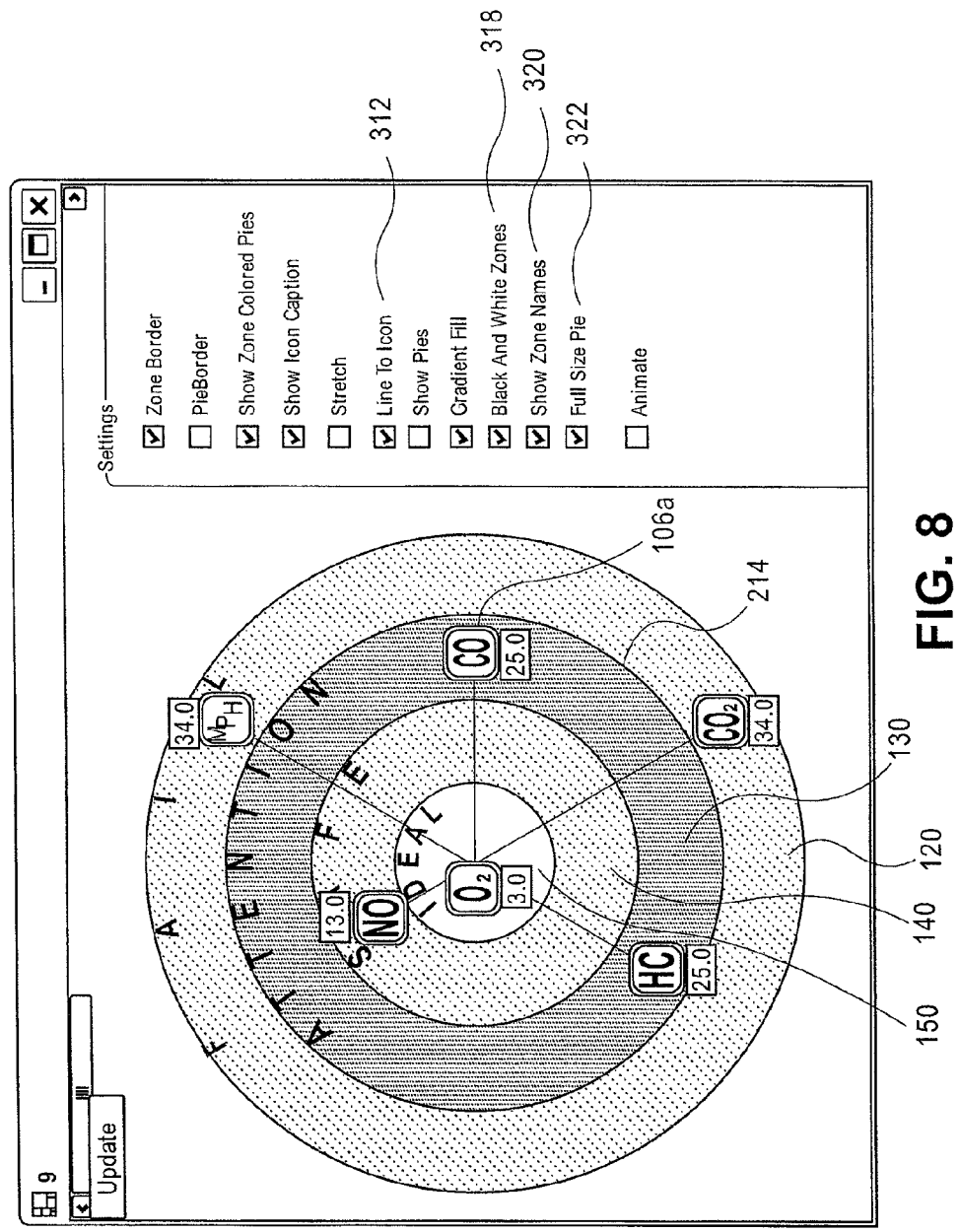
FIG. 8 is a graph of the vehicle health graphics on a display of a computing device such as personal computer or diagnostic tool depending on the selected options.

The black and white zones option 318, as seen in FIG. 8, has the zones being shown as black and white, as an example of an alternative color scheme for the zones. Therefore, as seen from zones 120 to 150, the zones alternate from white to black to white and back to black. The black portion can be a certain gray scale accommodating for an optimal viewing by the technician. This scheme can accommodate for certain technicians a better reading from a distance as they can better differentiate the changes in zones.

Referring to FIG. 8, the "show zone names" option 320 indicates if names are given to the zones, then they are displayed in the appropriate zone.

A full size pie option 322 is shown in FIG. 8. The pie is drawn to the edge of the display area instead of only to the reach of the value. This is done as a preference of the technician on seeing the whole pie or only to where the reach of the value is shown. Showing the whole pie, for example, can give a better perspective to the technician of the value depicted on the chart in relation to the norm. However, for certain reasons, the technician may not want to see the whole pie, and only up to the value shown. This can be necessary, for example, if the display is limited, or the values shown need to be shown with a greater magnification for the technician to see.

The animation option 324 permits the sample shown, for example, FIGS. 5-8, to be animated with random values or the animation can show other changes in the chart in real-time or delayed time.

The invention can be realized as computer-executable instructions in computer readable media as shown in FIG. 4. The computer readable media includes all possible kinds of media in which computer readable data is stored or included or can include any type of data that can be read by a computer or a processing unit. The computer readable media include for example and not limited to storing media, such as magnetic storing media (e.g., ROMs, floppy disks, hard disk, and the like), optical reading media (e.g., CD ROMs (compact disc-read-only memory), DVDs (digital versatile discs), re-writable versions of the optical discs, and the like), hybrid magnetic optical disks, organic disks, system memory (read-only memory, random access memory), non-volatile memory such as flash memory or any other volatile or non-volatile memory, other semiconductor media, electronic media, electromagnetic media, infrared, and other communication media such as carrier waves (e.g., transmission via the Internet or another computer). Communication media generally embodies computer-readable instructions, data structures, program modules or other data in a modulated signal such as the carrier waves or other transportable mechanism including any information delivery media. Computer-readable media such as communication media may include wireless media such as radio frequency, infrared microwaves, and wired media such as a wired network. Also, the computer-readable media can store and execute computer-readable codes that are distributed in computers connected via a network. The computer readable medium also includes cooperating or interconnected computer readable media that are in the processing system or are distributed among multiple processing systems that may be local or remote to the processing system. The invention can include the computer-readable medium having stored thereon a data structure including a plurality of fields containing data representing the techniques of the invention.

Figure 9:
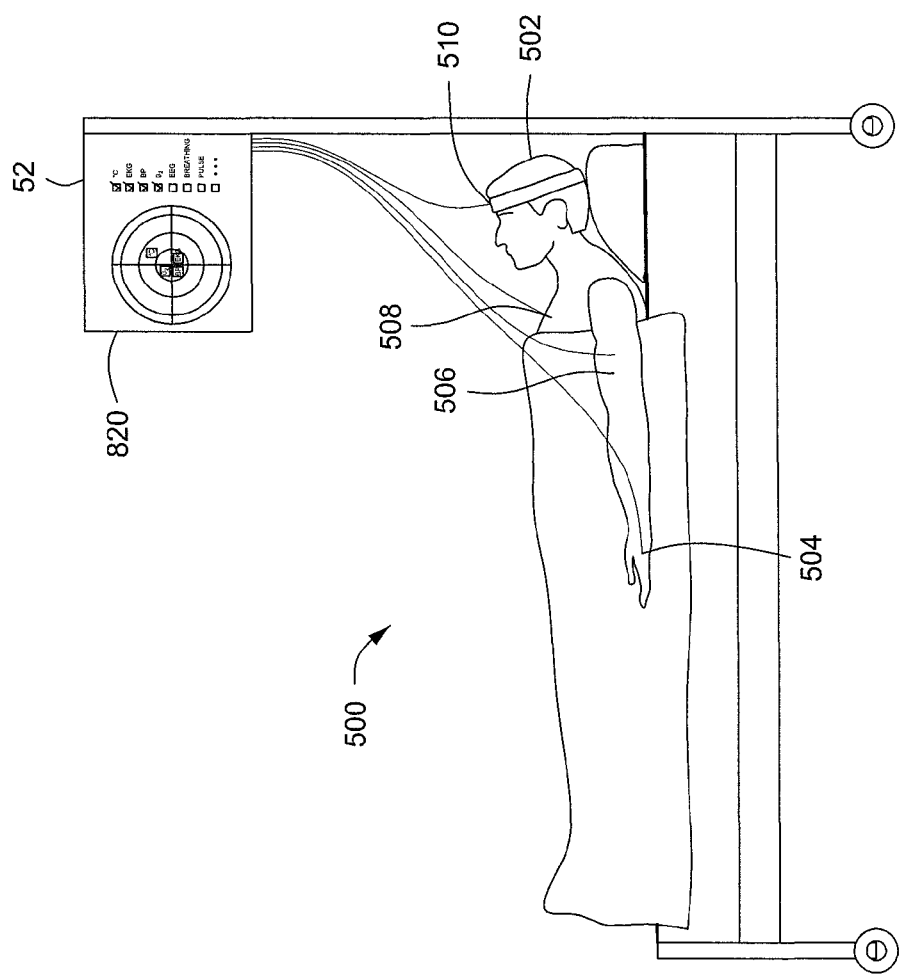
FIG. 9 is an illustration of a system for displaying a set of diagnostic values for a patient in accordance with another embodiment of the invention.

FIG. 9 is an illustration of a system 500 for displaying a set of diagnostic values for a patient 502 in accordance with another embodiment of the invention. As shown in FIG. 9, the system 500 is configured to collect any suitable diagnostic values from the patient 502. Examples of suitable diagnostic values include blood $O_2$ levels, pulse, temperature, blood pressure, breathing rate, electroencephalogram readings, electrocardiogram readings, and the like. By way of some particular examples, blood $O_2$ may be sensed via a blood $O_2$ meter 504 disposed upon the patient's finger, blood pressure may be sensed via an automated blood pressure cuff 506, heartbeat information may be sensed by an electrocardiogram sensor 508, electrical activity of the brain may be sensed by an electroencephalogram sensor 510, and the like. These sensors 504-510 sense various attributes of the patient 502 which are conveyed to the computer 52 and displayed on the display 820 as described herein.

Figure 10:
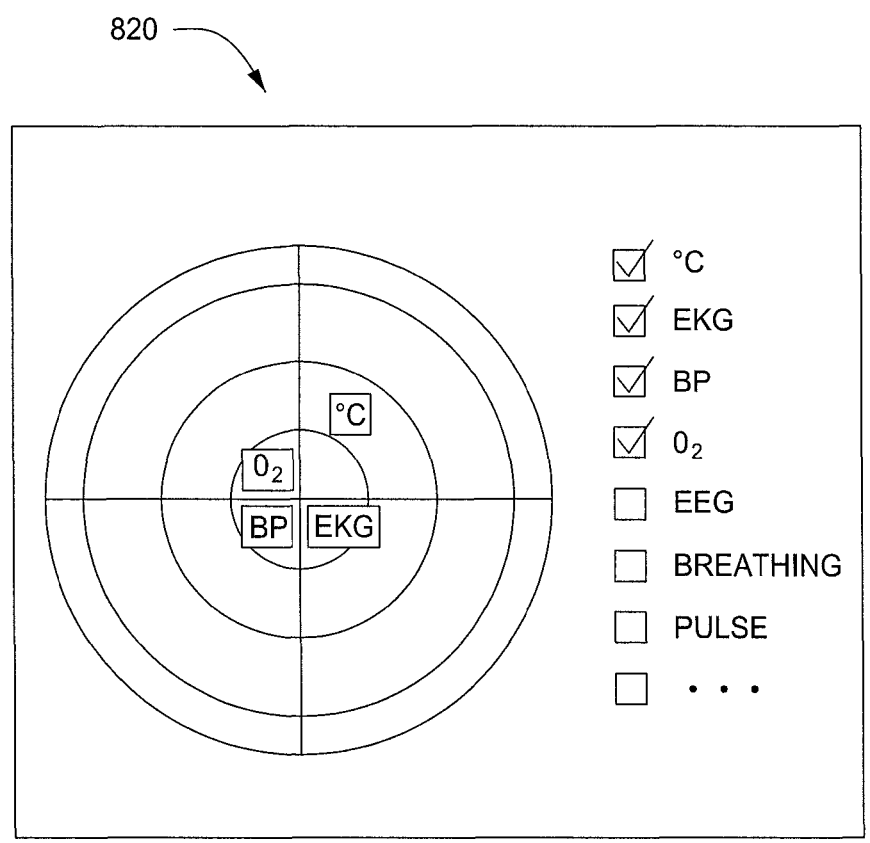
FIG. 10 is a graph of the health graphic on a display of a computing device such as personal computer or diagnostic tool depending on the selected options according to the embodiment of FIG. 9.

FIG. 10 is a screen capture of the display 820 configured to display the diagnostic values according to the embodiment of FIG. 9. As shown in FIG. 10, various diagnostic values may be selected for display. If selected, a check mark or other indication may appear in the selected box and the associated values may be displayed. As already described herein, a corresponding icon for each of the diagnostic values may be displayed relatively closer to a center of the display 820 in response to the diagnostic value being relatively close in value to a predetermined normal value. In response to a diagnostic value deviating from its corresponding normal value, the corresponding icon is displayed outside of the center. The further the diagnostic value deviates from its corresponding normal value, the further from the center the corresponding icon is displayed. In this manner, several diagnostic values may be quickly and easily interpreted.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of displaying information, comprising:
receiving via a computing device a set of diagnostic values for a patient;
comparing via a processor of the computing device the set of diagnostic values with a set of predetermined normal values;
displaying on a display a video image having a graphical depiction of the set of diagnostic values in comparison to the set of predetermined normal values, with the set of predetermined normal values being displayed in a predetermined region of the video image, and the set of diagnostic values being displayed in the video image in relation to the predetermined region of the set of predetermined normal values; and
indicating varying levels of relative health of the patient according to a placement of an icon relative to areas of the graphical depiction of the set of diagnostic values,
wherein the video image includes the set of diagnostic values being displayed relatively closer to a portion of the display in response to the set of diagnostic values being relatively closer to values of the set of predetermined normal values.

2. The method of claim 1, wherein the icon includes a value indicating the set of diagnostic values of a health of the patient.

3. The method of claim 1, wherein the video image further comprises the graphical depiction of values having a dependency on a location within the display to indicate a comparison to the set of predetermined normal values.

4. The method of claim 1, wherein the video image is sectioned into a plurality of concentric circles with the set of diagnostic values being located according to the comparison to the set of predetermined normal values, and the plurality of concentric circles being sectioned further into a plurality of subdivisions, with each subdivision representing an additional dependency on a predetermined variable.

5. The method of claim 1, wherein the video image comprises regions of at least one of coloring and shading according to a deviation from the set of predetermined normal values.

6. The method of claim 1, wherein the video image comprises different regions divided according to a set range of deviations from the set of predetermined normal values.

7. The method of claim 1, wherein the video image includes alterations of the video image according to the display of the set of diagnostic values as compared to the set of predetermined normal values.

8. The method of claim 1, wherein the video image includes a plurality of icons representing particular measured variables of the patient and the set of diagnostic values being displayed adjacent to the respective icons, and the icons and the set of diagnostic values being moved around a concentric circle at a same distance from a center of the concentric circle in order to not overlap a displayed image of the icon and related diagnostic value.

9. The method of claim 1, wherein the steps of the method comprise a set of computer executable instructions stored on a computer readable media.

10. An apparatus for displaying a patient's diagnostic values, comprising:
a communication interface to receive diagnostic values;
a memory to store a set of computer executable instructions for displaying of the diagnostic values;
a processor connected to the memory and being configured to execute the set of computer executable instructions, in response to the set of computer executable instructions, the processor being configured to compare the diagnostic values with a set of predetermined normal values;
a display displaying a video image having a graphical depiction of the diagnostic values in comparison to the set of predetermined normal values; and
an icon configured to indicate varying levels of relative health of a patient and positioned on the graphical depiction of the diagnostic values,
wherein the video image includes the diagnostic values being displayed relatively closer to a portion of the display in response to the diagnostic values being relatively closer to values of the set of predetermined normal values.

11. The apparatus of claim 10, wherein the icon includes a value indicating the diagnostic values of a health of the patient.

12. The apparatus of claim 10, wherein the video image further comprises a video depiction of the values having a dependency on a location within the display to indicate the comparison to the set of predetermined normal values.

13. The apparatus of claim 10, wherein the video image is sectioned into a plurality of concentric circles with the diagnostic values being located according to the comparison to the set of predetermined normal values, and the plurality of concentric circles being sectioned further into a plurality of subdivisions, with each subdivision representing an additional dependency on a predetermined variable.

14. The apparatus of claim 10, further comprising at least one of coloring and shading different regions of the video image according to a deviation from the set of predetermined normal values.

15. The apparatus of claim 10, further comprising dividing different regions of the video image according to a set range of deviations from the set of predetermined normal values.

16. The apparatus of claim 10, further comprising altering the video image according to the display of the diagnostic values as compared to the set of predetermined normal values.

17. The apparatus of claim 10, wherein the video image includes a plurality of icons each representing a particular type of diagnostic value of the diagnostic values and the diagnostic values being displayed adjacent to the respective icons, and the icons and the diagnostic values being moved around a concentric circle at a same distance from a center of the concentric circle in order to not overlap a displayed image of the icon and related diagnostic value.

18. A system for displaying a set of diagnostic values from a patient, the system comprising:
a means for receiving the set of diagnostic values;
a means for comparing the set of diagnostic values with a set of predetermined normal values;
a means for displaying a video image having a graphical depiction of the set of diagnostic values in comparison to the set of predetermined normal values; and
an icon configured to indicate varying levels of relative health of the patient and positioned on the graphical depiction of the set of diagnostic values,
wherein the video image includes the set of diagnostic values of the patient being displayed relatively closer to a portion of the means for displaying in response to the set of diagnostic values being relatively closer in value to the set of predetermined normal values.

19. The system of claim 18, wherein the icon includes a value indicating diagnostic values of health of the patient.

20. The system of claim 18, wherein the video image further comprises a video depiction of the values having a dependency on a location within the means for displaying to indicate the comparison to the set of predetermined normal values.

* * * * *